United States Patent [19]

Stitt

[11] Patent Number: 5,313,858
[45] Date of Patent: May 24, 1994

[54] RUBBER STOPPER REMOVER

[75] Inventor: Robert R. Stitt, Arvada, Colo.

[73] Assignee: Midwest Research Institute, Kansas City, Mo.

[21] Appl. No.: 28,691

[22] Filed: Mar. 8, 1993

[51] Int. Cl.⁵ ............................................. B67B 7/16
[52] U.S. Cl. .................................... 81/3.55; 81/3.09; 81/3.27
[58] Field of Search .................. 81/3.55, 3.07, 3.08, 81/3.09, 3.25, 3.27, 3.4, 3.41, 3.44, 3.47, 3.56, 3.48, 3.49, 64

[56] References Cited

U.S. PATENT DOCUMENTS

| | | | |
|---|---|---|---|
| 2,338,753 | 1/1944 | Flessner | 81/3.55 |
| 2,510,459 | 6/1950 | Bloomfield et al. | 81/3.55 |
| 2,516,436 | 7/1950 | Whiteley | 81/3.55 |
| 3,048,068 | 8/1962 | Griffiths | |
| 3,583,263 | 6/1971 | Herigstad | |
| 4,073,205 | 2/1978 | Silliman | 81/3.09 |
| 4,509,784 | 4/1985 | Vollers | 81/3.44 X |
| 4,846,024 | 7/1989 | Bryant et al. | |

FOREIGN PATENT DOCUMENTS 2910100  9/1980  Fed. Rep. of Germany ......... 81/3.4

Primary Examiner—D. S. Meislin
Attorney, Agent, or Firm—Ken Richardson

[57] ABSTRACT

A device for removing a rubber stopper from a test tube is mountable to an upright wall, has a generally horizontal splash guard, and a lower plate spaced parallel to and below the splash guard. A slot in the lower plate has spaced-apart opposing edges that converge towards each other from the plate outer edge to a narrowed portion, the opposing edges shaped to make engagement between the bottom of the stopper flange and the top edge of the test tube to wedge therebetween and to grasp the stopper in the slot narrowed portion to hold the stopper as the test tube is manipulated downwardly and pulled from the stopper. The opposing edges extend inwardly to adjoin an opening having a diameter significantly larger than that of the stopper flange.

9 Claims, 2 Drawing Sheets

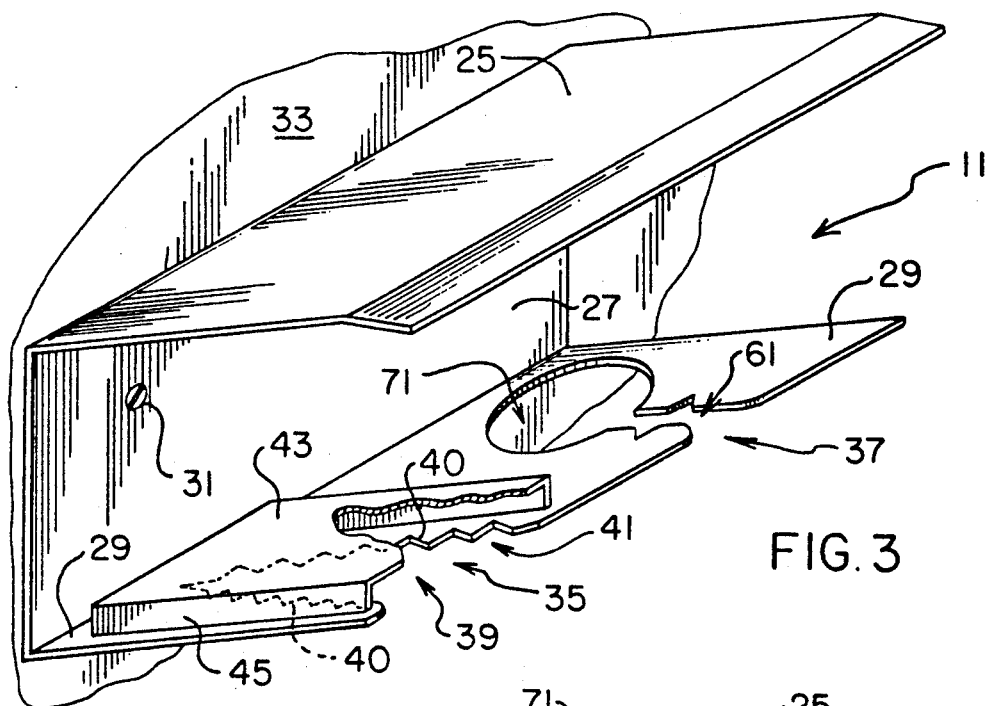
FIG. 3
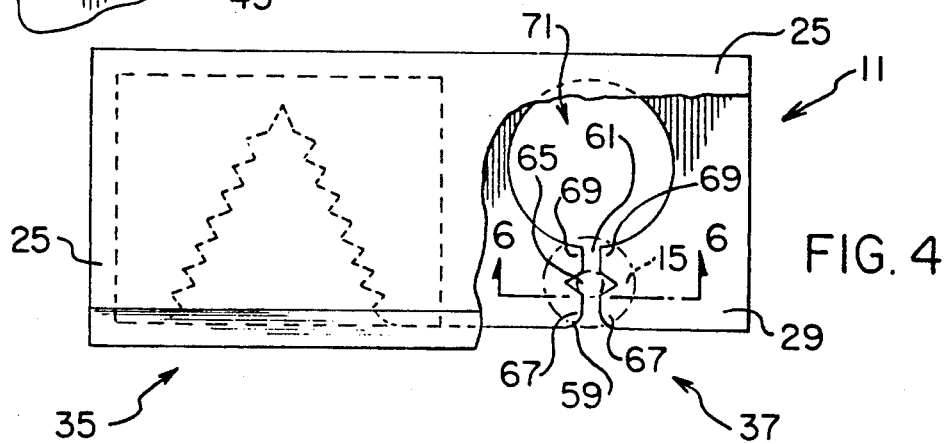
FIG. 4
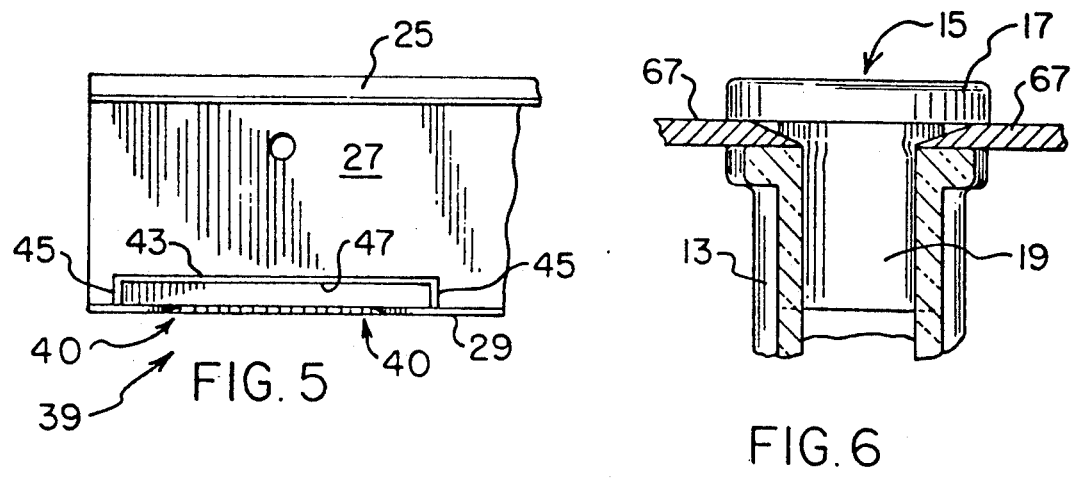
FIG. 5
FIG. 6

RUBBER STOPPER REMOVER

CONTRACTUAL ORIGIN OF THE INVENTION

The U.S. Government has rights in this invention under Contract No. DE-AC02-83CH10093 between the U.S. Department of Energy and the National Renewable Energy Laboratory, a Division of the Midwest Research Institute.

BACKGROUND OF THE INVENTION

1. Field of the Invention

The present invention relates to devices for facilitating the removal of flange-topped rubber stoppers from installed positions within test tubes and like vessels.

2. DESCRIPTION OF THE PRIOR ART

So-called "anaerobic" tubes and flasks are heavy-duty Pyrex glass vessels that are used in the laboratory, and it is often necessary to plug the mouth of such a vessel to seal its pressurized contents, most commonly with a conventional rubber stopper that has a circular flange top for grasping, and a cylindrical lower portion for insertion within the vessel mouth. To ensure that the stopper is not dislodged by internal pressure, it is a common practice to apply a metallic retainer, such as an aluminum crimp seal that covers the stopper top and engages the underside of a lip that extends about the periphery of the top of the vessel. When experiments are completed and laboratory equipment set-ups are to be disassembled, the anaerobic vessels must be unplugged for cleaning and made available for reuse. This is typically accomplished by first removing the metal retainer by grasping the retainer's integral tear tab and then tearing it off so as to sever the hold of the retainer. Here, one must be cautious to avoid injury to the fingers by sharp metallic edges presented by the broken retainer. Then using both hands, the stopper flange is pried upwardly with the thumb to urge the stopper from the mouth of the vessel. All too often, a stopper will become stuck in place, and removal of such a stopper by hand will become a difficult, time-consuming task. Even when a stuck stopper is not encountered, the unplugging of several test tubes will often cause a bothersome soreness at the thumb tip, and sometimes tearing of the skin. At other times, particularly when there is difficulty in prying the stopper loose, the rim of the tube will break. Besides representing an equipment loss, jagged edges of a broken vessel and sometimes flying glass present an obvious immediate safety hazard to the handler. Such accidents can be particularly serious when toxic contents are involved.

Oftentimes test tube reactants will generate high-pressure gaseous by-products. In order to relieve this pressure prior to stopper removal, it is the prescribed practice to first pierce the stopper with a syringe to relieve the pressure. Unfortunately, through human error and oversight, occasionally some vessels will not be depressurized. In such cases, unplugging of the vessels will be occasioned by expelling of the liquid and gaseous contents. In some cases, when the metal retainer is removed, the unrestrained stopper will immediately be forcefully propelled from the vessel, followed by the pressurized contents. This can also be particularly hazardous when the contents are harmful substances.

SUMMARY OF THE INVENTION

In view of the aforestated drawbacks of the prior art, it is a general object of the present invention to provide an improved way for removing flange-topped stoppers from the ends of "anaerobic" test tubes, and the like.

Another object of the present invention is to provide for the quick and easy removal of such stoppers from laboratory vessels.

Yet another object of the invention is to provide a means to remove stoppers in a way that minimizes breakage and which minimizes harm to the handler when pressurized contents are discharged from the opened vessel.

Still another object of the invention is to provide a safe, effective and easy way to remove the metal retainers, as well as the stoppers.

These, and other objects and advantages, are provided by the present invention, a device that assists removal of a rubber flange-topped stopper from its installed position in the mouth of a glass vessel, wherein the stopper has a cylindrical stem extending down from its flange top, and the flange top of the installed stopper abuts the top of the vessel. The device structure includes an integral support web that is adapted to be fastened stationarily to an upright wall, and a splashguard extending outwardly from the upper part of the support web. Extending from a lower part of the support web and spaced generally parallel to the splash guard is a lower plate that has an outer edge and an opening in the outer edge defined by spaced-apart opposing tapered edges that converge with respect to each other to a narrowed spacing, the opposing tapered edges being adapted to be engaged like a wedge between the lower surface of the stopper flange and the top of the glass vessel. The narrowly spaced opposing tapered edges are adapted to frictionally embrace the stopper stem. Further inwardly from the narrowed portion, and continuing therefrom, is a relatively large opening having a diameter that is significantly greater than that of the flange top of the stopper.

In a variant of the invention the lower plate includes additional structure, adapted for removing the metal retaining cap from the stopped vessel prior to removal of the stopper, in a quick, safe, and effective manner. Opposing edges that are serrated converge to form a V-notch. Positioned above the plane of the V-notch at a predetermined parallel spacing is a depth plate having a surface adapted to be slidably abutted by the top surface of a retainer-equipped test vessel. These converging edges are adapted to deformingly press into opposite sides of the metal retaining cap as the cap is moved laterally into their grasp, and to retain the cap for subsequent prying off.

BRIEF DESCRIPTION OF THE DRAWINGS

The accompanying drawings, which are incorporated in and form a part of the specification, illustrate a preferred embodiment of the present invention and together with the description, serve to explain the principles of the invention, wherein:

FIG. 3 is a perspective view of a device according to the present invention;

FIG. 4 is a top plan view, with parts broken away for clarity, of a device according to the present invention;

FIG. 5 is a partial, front elevational view of a device according to the present invention; and FIG. 6 is a partially sectional view taken along the line 6—6 of FIG. 4.

DETAILED DESCRIPTION OF THE INVENTION

Figure 2:
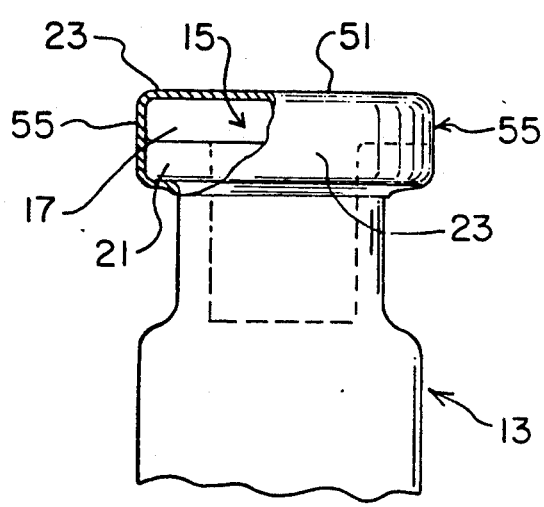
FIG. 2 is a partial, side elevational view, with parts broken away, of a vessel equipped with a stopper and a metallic retaining cap.
Figure 1:
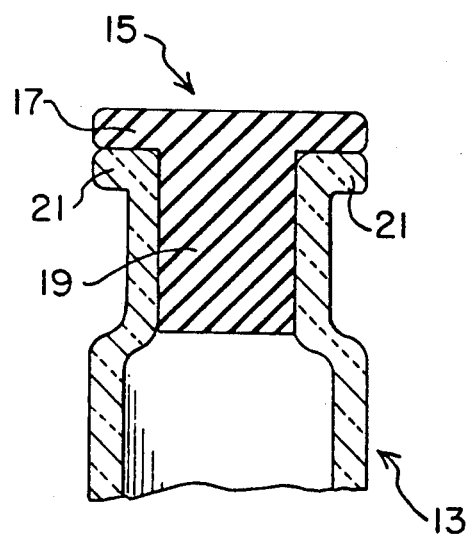
FIG. 1 is a partial, sectional elevational view of the upper part of a laboratory vessel equipped with a flange-topped rubber stopper.

FIGS. 1 and 2 show the upper portion 13 of a typical Pyrex glass "anaerobic" laboratory vessel, such as a test tube or bottle, and a typical rubber stopper 15 that has a flange top 17 and lower portion 19 that is fully inserted in the vessel. FIG. 1 best shows how the upper surface of vessel lip 21 abuts the lower surface of flange top 17, the outside diameter of lip 21 being approximately the same as that of the flange top 17. In most laboratory applications it is common for a pliable aluminum retainer 23 to be crimped in place over the installed stopper 15 as FIG. 2 illustrates, retainer 23 engaging the underside of lip 21 to hold against upward movement. It is for laboratory vessels that are sealed in this manner that the preferred embodiment of the invention, to be described, is particularly adept at removing retaining caps and stoppers in an expeditious and safe manner.

Referring now to FIGS. 3 and 4, a preferred embodiment of the present invention is shown in the form of device 11 which will now be described. Device 11, which is fabricated of metal using conventional metalworking techniques, essentially comprises a splash guard 25, a web portion 27, and a lower plate 29. Guard 25 and lower plate 29 are each rigidly affixed to the web portion 27, and each extends generally horizontally, or at a small upward incline, from web 27 which is equipped with holes through which conventional fasteners 31 can be applied to secure device 11 firmly to a vertical wall structure 33.

The plate 29 supports a cap-removing structure 35 and a stopper removing structure 37.

The cap-removing structure 35 features a V-slot 39 that has converging edges 40 that are tapered and provided with serrations 41. There is a depth plate 43 secured to the lower plate 29 at its opposing sides 45 by welding, and as FIG. 5 best shows, the depth plate 43 covers the V-slot 39 with the lower surface 47 shown in FIG. 5 of the depth plate 43 lying parallel to, and spaced a preselected distance from, the plane of the V-slot.

The structure 35 is adapted to receive the top of the retainer-capped vessel shown in FIG. 2, and in using the invention it is intended that the top surface 51 of the retaining cap be held flush in sliding contact with lower surface 47 as the capped top is moved laterally into the grasp of the converging edges 40. In this regard it is noted that the spacing between surface 47 and the plane of the V-slot is selected such that the slot edges 40 will impinge the metal foil of the cap at an approximate location 55 shown in FIG. 2 that is at elevation higher than the top of the glass lip 21 and subtended by the resiliently deformable flange 17. Thus pressure will not be exerted against glass as the slot edges 40 engage the cap and as they deformingly bite into and depress the aluminum foil covering the sides of flange 17. When the retaining cap is thusly engaged, the vessel can be pivoted in a lever-like manner, laterally, to cause the secured cap to be readily pried from the vessel top. With the retainer removed the vessel top has the configuration shown in FIG. 1 and then can be applied to structure 37, to be described, for the quick, safe removal of stopper 19.

The stopper removing structure 37 features opposing tapered edges 59 that converge toward each other from the outer edge of plate 29, to a narrowed region at 61 where opposing tapered edges lie generally parallel to each other and spaced a distance apart that is chosen to be slightly narrower than the stem 19 of stopper 15. Note in FIG. 4 that each opposing edge has a recessed portion 65. This divides the opposing edges into first opposing edge pairs 67 at the forefront of the narrowed region 61, and a rearward set of opposing edges 69. The narrowed region 61 opens rearwardly to a circular opening 71 that has a diameter that is significantly larger than that of the stopper flange top 17. Note that the leading portions of converging edges 59 as well as opposing edge pairs 67 and 69 are designed to make engagement between the bottom of flange 17 and the top surface of the glass lip 21, and as such they are tapered to form edges that are sufficiently narrow to facilitate insertion in the relatively narrow spacing under the flange 17.

As to the manner of use of structure 37, the tube to be unstopped is held generally upright, and the junction of the vessel top and the flange is aligned with the edges 59. Then the vessel is moved laterally so that edges 59 are wedged between the bottom of flange 17 and the top of the vessel. The vessel can then be further pushed to reach the fully inserted position illustrated in broken lines in FIG. 4, and in FIG. 6. Here the stopper 15 is frictionally held as shown, centrally between the opposing edge pairs 67 and 69, the spaced-apart fore-edges 67 resiliently deforming a forward side of the rubber stem 19, and the aft opposing edge pair 69 similarly engaging a rearward side of rubber stem 19, with the resulting tendency to hold stopper 15 centrally positioned. With the stopper 15 thusly held, the handler can manipulate the test tube downwardly and completely free it from the neck 13 of the vessel. The freed stopper will be retained in place between the opposing edge pairs 67 and 69. When a stopper is to be removed from another vessel, the flange of this other stopper will abut the flange 17 of the stopper that is already held in structure 37, and insertion of the second stopper in structure 37 will push the first stopper beyond the narrowed region 61 and into the opening 71, through which it will fall for collection by suitable means below.

While a particular embodiment of the invention has been described herein, it is not intended that the invention be limited thereto, since various modifications and changes may readily occur to those skilled in the art without departing from the invention. Therefore it is aimed to cover all such changes and modifications as fall within the true spirit and scope of the invention as defined in the claims that follow.

The embodiments in which an exclusive property or privilege is claimed are defined as follows:

1. Device for removing a rubber stopper from its installed position in the end of a glass tube, said rubber stopper having a generally cylindrical stem and a flange top, said device including:

a. a support web adapted to be fastened to a wall surface;

b. a splash guard extending generally horizontally and outwardly from said support web;

c. a lower plate extending outwardly from said support web and spaced a predetermined distance below said splash guard, and having an outer edge, said plate having an opening extending inward from said outer edge, said opening characterized by first and second spaced-apart tapered opposing edges that converge toward each other to a narrowed portion of narrowly spaced edges;

d. an opening larger than said flange top, in said lower plate, inward of, and adjoining said narrowly spaced edges.

2. Device as defined in claim 1 wherein each of said narrowly spaced-apart opposing edges has a recessed portion therein.

3. Device as defined in claim 1 wherein said tapered opposing edges have wedge-shaped cross-sectional configurations and are adapted to be wedged between said flange and said glass tube.

4. Device as defined in claim 2 wherein said narrowly spaced-apart edges have a first, forward opposing edge-pair, and a second, rearward opposing edge pair.

5. Device as defined in claim 1 wherein the spacing between said narrowly spaced edges is less than the diameter of said stopper stem, whereby said stem is resiliently grasped and deformed by said narrowly spaced edges when said narrowly spaced edges are inserted between said flange top and the end of said glass tube.

6. Device as defined in claim 5 wherein said narrowly spaced edges have a first, forward opposing edge-pair, and second, rearward opposing edge pair, and said first and second edge pairs are adapted to engage respectively, opposite first sides of said stopper stem, and opposite second sides of said stopper stem when said narrowly spaced edges are inserted between said flange top and the end of said glass tube.

7. Device as defined in claim 1 wherein said rubber stopper in its installed position is covered by a soft metallic retaining cap, and said device further including structure on said lower plate for removing said cap, and said structure including a V-slot with a pair of spaced-apart converging sides adapted to engage said cap, and a depth plate, parallel to said lower plate and spaced a predetermined distance above the plane of said V-slot.

8. Device as defined in claim 7 wherein each of said sides has a plurality of serrations.

9. Device as defined in claim 1 wherein said lower plate opening is circular and has a diameter larger than the diameter of said stopper flange top.

* * * * *